(12) United States Patent
Yates et al.

(10) Patent No.: US 8,906,965 B2
(45) Date of Patent: *Dec. 9, 2014

(54) ANTI-INFLAMMATORY QUINIC ACID DERIVATIVES FOR RADIOPROTECTION/RADIOMITIGATION

(75) Inventors: Charles Ryan Yates, Collierville, TN (US); Duane Douglas Miller, Germantown, TN (US); Mostafa Waleed Gaber, Bellaire, TX (US); Karin Emmons Thompson, Marion, AR (US); Kui Zeng, Scottsdale, AZ (US); Jordan J. Toutounchian, Memphis, TN (US)

(73) Assignee: The University of Tennessee Research Foundation, Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/320,540

(22) PCT Filed: May 11, 2010

(86) PCT No.: PCT/US2010/034450
§ 371 (c)(1),
(2), (4) Date: Jun. 6, 2012

(87) PCT Pub. No.: WO2010/132504
PCT Pub. Date: Nov. 18, 2010

(65) Prior Publication Data
US 2012/0283331 A1 Nov. 8, 2012

Related U.S. Application Data

(60) Provisional application No. 61/177,001, filed on May 11, 2009.

(51) Int. Cl.
*A61K 31/16* (2006.01)
*A61K 31/015* (2006.01)

(52) U.S. Cl.
CPC .................................. *A61K 31/015* (2013.01)
USPC ......................................................... 514/612

(58) Field of Classification Search
USPC ......................................................... 514/612
See application file for complete search history.

(56) References Cited

U.S. PATENT DOCUMENTS

| 2,771,487 A | 11/1956 | Morris et al. |
| 4,938,949 A | 7/1990 | Borch et al. |
| 8,115,031 B2 | 2/2012 | Yates et al. |
| 2005/0065210 A1 | 3/2005 | Ackermann et al. |
| 2007/0025933 A1 | 2/2007 | Gomez-Pamo et al. |

OTHER PUBLICATIONS

U.S. Appl. No. 14/074,457, Yates et al.
Nguyen et al. Synthesis and NMR-characterization of three qinamide-based disaccharide mimetics with unusual cyclohexame twistconformation. ARKIVOC 2005 (iv) 110-128; p. 111, para 1; p. 112, Scheme 2.
Written Opinion in the related PCT/US10/34450, 2010.
Kaila et al. 2005 J. Med. Chem. 48:4346-4357.
Hanessian S. et al. 1997 J. Org. Chem 62:465-473.
Adachi et al. 2003 Biosci. Biotechnol. Biochem. 67:2124-2131.

*Primary Examiner* — Zohreh Fay
(74) *Attorney, Agent, or Firm* — Lihua Zheng; Mary S. Consalvi; Proskauer Rose LLP

(57) ABSTRACT

Disclosed are methods of use of analogs of quinic acids or shikimic acids for protection from the harmful effects of radiation when administered either prior to radiation exposure, after radiation exposure, or both. These methods are useful for treating humans and animals exposed to radiation and at risk for radiation sickness and/or death as the result of radiation exposure.

10 Claims, 16 Drawing Sheets

US 8,906,965 B2

ANTI-INFLAMMATORY QUINIC ACID DERIVATIVES FOR RADIOPROTECTION/RADIOMITIGATION

CROSS-REFERENCE TO RELATED APPLICATIONS

This application claims the benefit of priority of earlier-filed U.S. Provisional Patent Application No. 61/177,001, filed May 11, 2009, the disclosure of which is incorporated herein by reference.

FIELD OF THE INVENTION

The invention relates to quinic and shikimic acid derivatives. More specifically, the invention relates to amide derivatives of quinic acids and shikimic acids and to methods for their use as radioprotectant and radiomitigant compositions.

BACKGROUND OF THE INVENTION

Non-steroidal anti-inflammatory agents are prescribed to patients at a rate of approximately 70 to 100 million prescriptions a year. Approximately 30+ billion dollars are spent each year for the purchase of anti-inflammatory agents, and researchers are continually searching for new and better anti-inflammatory compositions. A significant percentage of human disease is considered to be "inflammatory disease" or is considered to have a significant inflammatory component as part of the causation or progression of the disease. Inflammatory diseases may affect any organ system, and although they may be more prevalent in older individuals, particular races, or may be more common in one gender, they can affect anyone. These diseases include neurodegenerative disorders, asthma, hepatitis, acute respiratory disorder (ARD), chronic obstructive pulmonary disease (COPD), hepatitis, rheumatoid arthritis, inflammatory bowel disease, multiple sclerosis, nephritis, glomerulonephritis, ischemia/reperfusion injury, septic shock, and sarcoidosis, just to name a few. The numbers of individuals who are affected by these diseases are significant. For example, approximately 15% of the population of the United States suffers from rheumatic disorders.

Recently, in large part due to the threat of terrorism, but also as the result of a desire to decrease illness related to radiation therapies, there has been an increased interest in the discovery of agents which may decrease cellular damage resulting from radiation exposure. Various groups have discovered that certain compounds having antioxidant and/or anti-inflammatory properties may also provide some degree of protection from radiation (i.e., these compounds are "radioprotectants," being effective to some degree when administered prior to radiation exposure). Flax seed and delta-tocotrienol fall into this category, for example.

It is, however, not always possible to know when radiation exposure may occur—or whether a measured dose may have unintended and unanticipated harmful effects. Therefore, it would be of great benefit to identify compounds which could safely be used as radiomitigants (i.e., effective for limiting radiation damage when administered after radiation exposure), as well as radioprotectants.

SUMMARY OF THE INVENTION

The invention relates to methods for protecting cells from radiation and for limiting radiation damage in cells exposed to radiation, the methods comprising administering one or more therapeutically effective doses of one or more radioprotectant/radiomitigant compositions which may be described as analogs of quinic acid and/or shikimic acid, such analogs having a structure as in Formula I

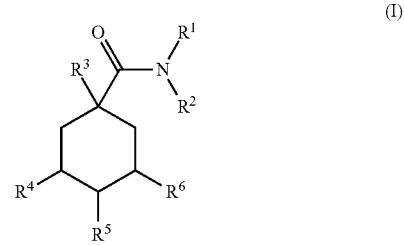

where:

$R^1$ and $R^2$ are each independently hydrogen, straight or branched alkyl, cycloalkyl, aryl, benzyl, arylalkyl, heterocyclic amine, aminoalkyl,

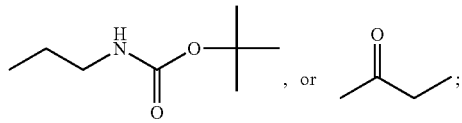

and $R^3$, $R^4$, $R^5$, and $R^6$ are each independently hydrogen or hydroxyl.

Compounds of the invention may also comprise compounds of Formula I where $R^3$ is substituted with

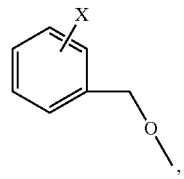

as well as compounds of Formula I where $R^3$ is absent and a double bond links carbons 1 and 6 of the ring.

In some aspects of the invention, compounds as described above may be administered to protect specific organs, subsets of cells, and/or organ systems, as well as to protect a human and/or animal and increase the survival rate of a population which has been exposed to ionizing radiation.

In various aspects, the method of the invention may encompass administering one or more compounds comprising quinic acid and/or shikimic acid analogs of Formula I for the prevention and/or treatment of radiation-induced cellular damage. The step of administering may be performed by various means, including, for example, oral and subcutaneous administration.

Another aspect of the invention is a method for inducing an anti-inflammatory effect in a human or animal, the method comprising administering to the human or animal a therapeutically effective amount of a compound of Formula I. In one aspect, the method for inducing an anti-inflammatory effect in a human or animal may comprise administering to the human or animal a compound of Formula I to decrease cellular NF-kB activity. In another aspect, the method for inducing an anti-inflammatory effect in a human or animal may comprise administering to the human or animal a compound of Formula I to decrease leukocyte adhesion.

DETAILED DESCRIPTION

Figure 1:
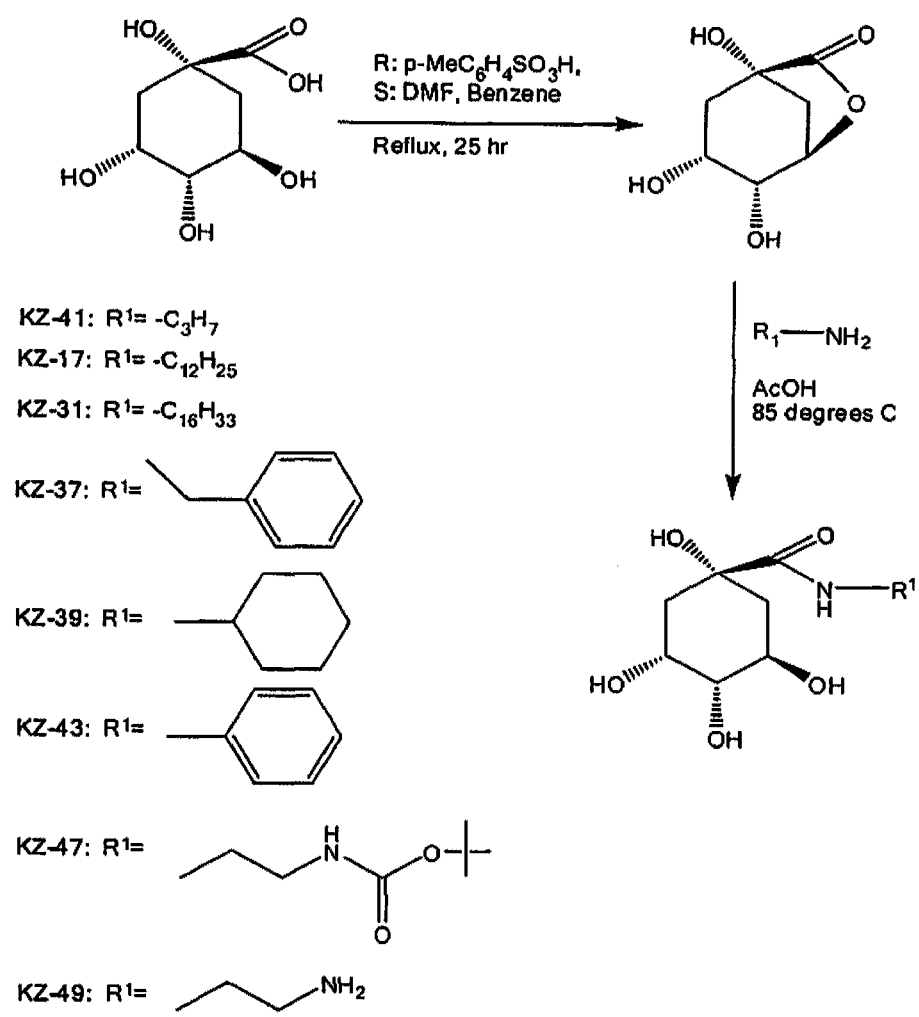
FIG. 1 is a scheme (Scheme 1) describing the synthesis of amides of the present invention. Amide groups for individual compounds are indicated by —NH—$R^1$, and $R^1$ is shown for each corresponding compound synthesized.
Figure 2:
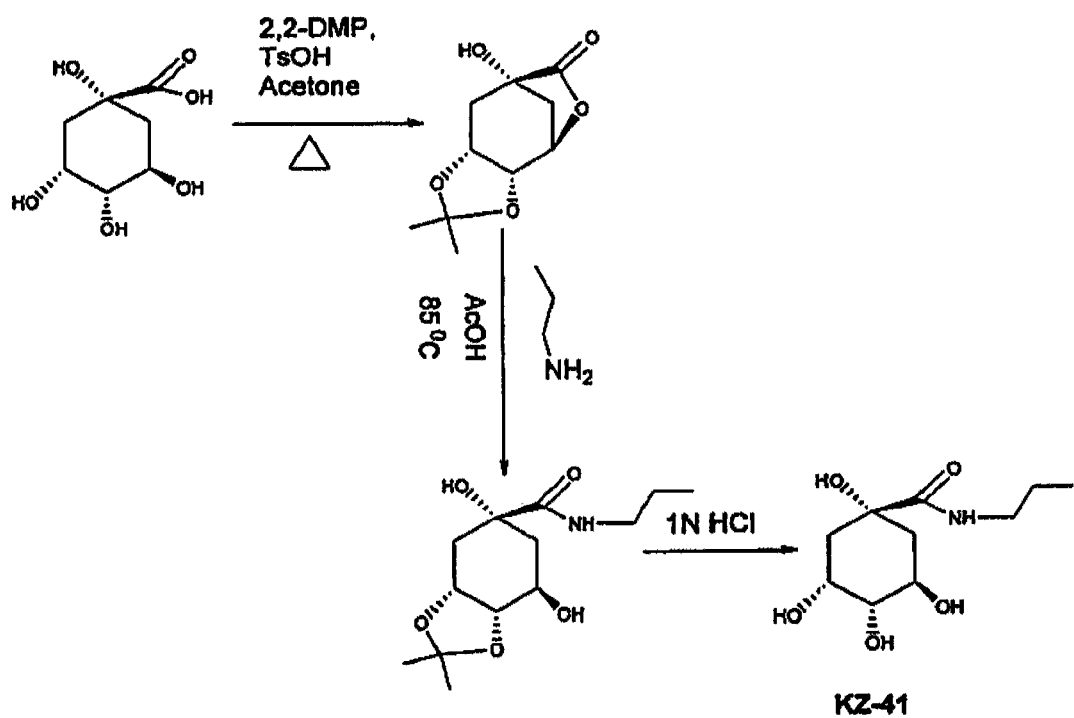
FIG. 2 is an alternate scheme (Scheme 2) for the synthesis of compound KZ-41.
Figure 3:
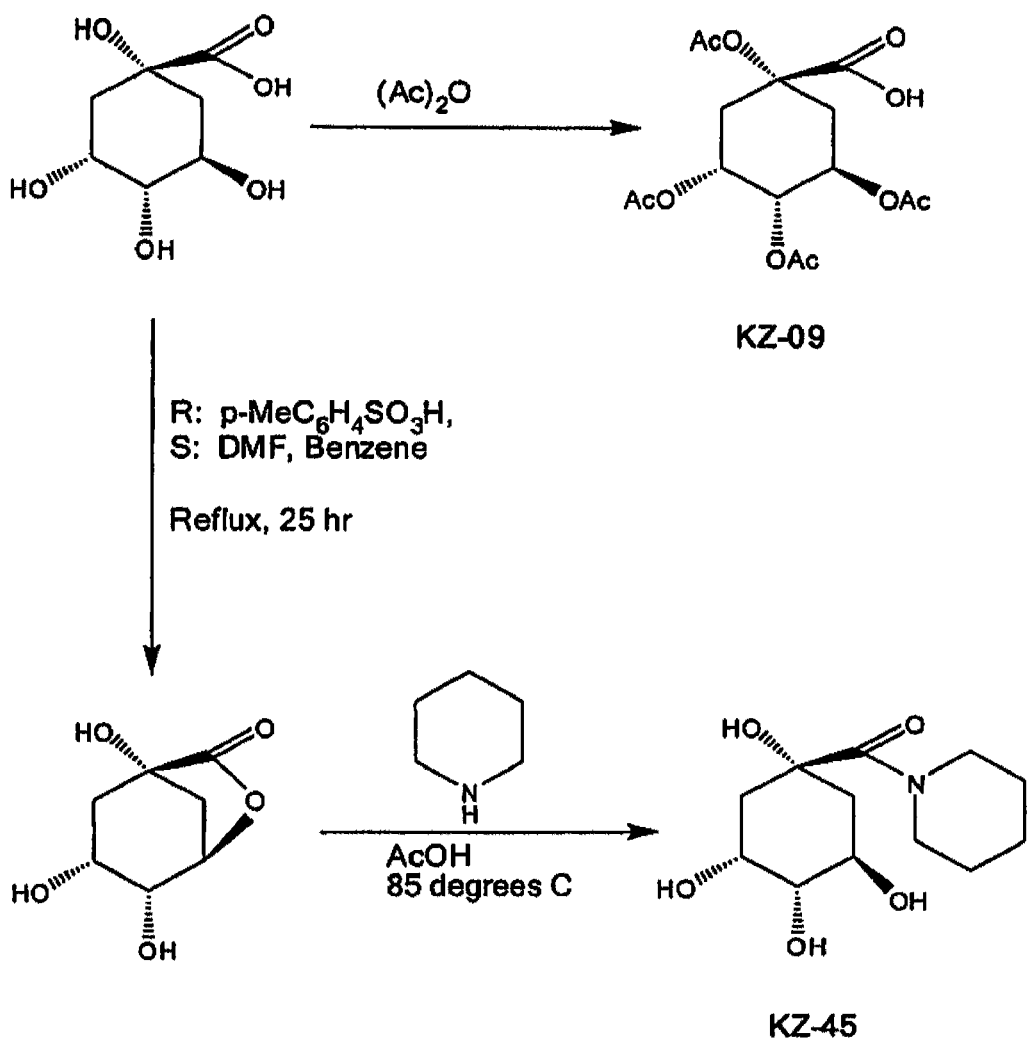
FIG. 3 is a scheme (Scheme 3) for the synthesis of compound KZ-09 and the heterocyclic amine-substituted KZ-45.

The inventors have synthesized derivatives of quinic acids and shikimic acids to provide compounds having significant anti-inflammatory activity. They designed these compounds for oral delivery, and studies using the MTS assay, a cell-proliferation assay that measures cytotoxicity, indicate that the compounds exhibit no cytotoxicity at 100 micromolar levels. The compounds are stable at room temperature, as well as being water-soluble. These compounds have previously been described in International Publication Number WO 2009/062200. More recently, the inventors have discovered that quinic acid and shikimic acid analogs are highly effective radioprotective and radiomitigant agents, providing a significant increase in 30-day survival in animals treated with a single dose administered 24 hours after radiation exposure. These compounds may therefore provide protection if administered before exposure to radiation. Even more importantly, the compounds are protective and therapeutic if administered after exposure. Administration of these compounds provides novel methods for improving cell, tissue, and organism survival following exposure to radiation. The compounds therefore provide important agents for the protection of individuals and populations which might be exposed during a nuclear event, as the result of workplace exposure, or as the result of therapeutic use of radiation for cancer treatment, for example.

As used herein, an "analog" is a structurally-related compound with a chemical similarity, but not necessarily having the same physical, chemical, biochemical, or pharmacological properties. In fact, the inventors believe that the modifications they have made to produce the analogs described herein have produced significantly improved biochemical and pharmacological properties, including, for example, making the compounds described herein more bioavailable when provided for oral administration. Also, the term "radiation" is intended to mean "ionizing radiation," examples of ionizing radiation including, but not being limited to, gamma-radiation sources and x-rays. A "radioprotective effect" is a decrease in radiation-induced damage to a cell, group of cells, organ, and/or organism when a radioprotective agent is administered prior to exposure of the cell, group of cells, organ, and/or organism (e.g., a human and/or animal) to radiation. A "radiomitigant effect" is a decrease in radiation-induced damage to a cell, group of cells, organ, and/or organism when a radiomitigant agent is administered after exposure of the cell, group of cells, organ, and/or organism (e.g., a human and/or animal) to radiation. Radiation-induced effects on cells, organs, humans, and animals have been documented and many such effects, such as the induction of certain cytokines, aberrations in cellular metabolism, DNA damage, and death, are known to those of skill in the art.

A "therapeutically effective amount" or "therapeutically effective dose" is an amount necessary to achieve the desired endpoint. One desired endpoint, for example, is rescue from radiation-associated mortality (i.e., survival). Additional desired endpoints may, for example, include decreased expression of inflammatory factors associated with cellular radiation damage, decreased occurrence of radiation sickness, hematopoietic syndrome, radiation-induced skin damage, etc. Assessment of a therapeutically effective amount is well within the skill of one in the medical and pharmaceutical arts, given the disclosure herein. For example, the U.S. Department of Health and Human Services Food and Drug Administration Center for Drug Evaluation and Research (CDER) has established guidance for estimating dosages (*Guidance for Industry: Estimating the Maximum Safe Starting Dose in Initial Clinical Trials for Therapeutics in Adult Healthy Volunteers*, July 2005). Therapeutically effective doses may be achieved via administration of a single dose, but may also be achieved via administration of more than one dose, such as an initial dose in combination with one or more additional doses which may be provided within a specific timeframe, for example, such as within about 12 to about 72 hours after the initial dose. Where dermal protection is desired, a therapeutically effective dose may be administered via one or more applications of a formulation suitable for topical application, such as a cream or lotion, for example, with the number and timing of the applications being determined by the individual applying the product, given the circumstances under which exposure to radiation is taking place.

Quinic acid may be synthesized by methods previously described in the literature, or may be isolated from a variety of plant extracts, such as Cat's Claw extract. These extracts have previously been shown to have anti-inflammatory properties, and subsequent research demonstrated that a significant portion of this activity is attributable to the quinic acid portion of the plant extract. Extracts have been used therapeutically for a variety of diseases including allergy, arthritis, chemotherapy side effects, cancer, bacterial/fungal infections, gastrointestinal inflammation and gastric ulcers. Oral administration of a hot water Cat's Claw extract, C-Med-100®enhanced all leukocyte populations in a doxorubicin-induced leucopenia rat model, whereas Neupogen®, a granulocyte colony stimulator commonly used to treat chemotherapy-induced leucopenia, increased only the neutrophil fraction.

Figure 12:
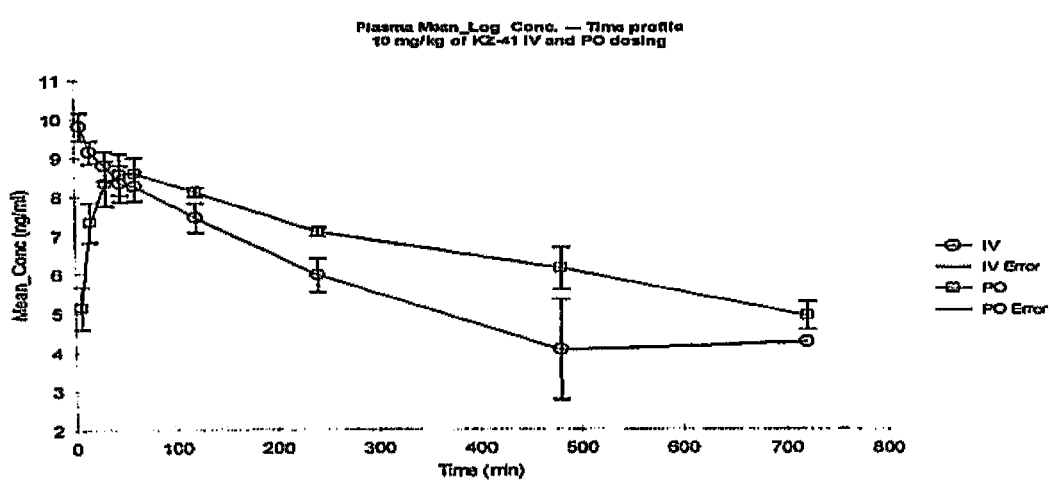
FIG. 12 is a graph illustrating the levels of analog KZ-41 when provided orally (PO), top line, or by intravenous administration (IV), bottom line. Unlike native or synthetic quinic acid, which is degraded by enzymes produced by bacteria in the intestines, KZ-41 is not degraded and is available for absorption into the circulation.
Figure 13:
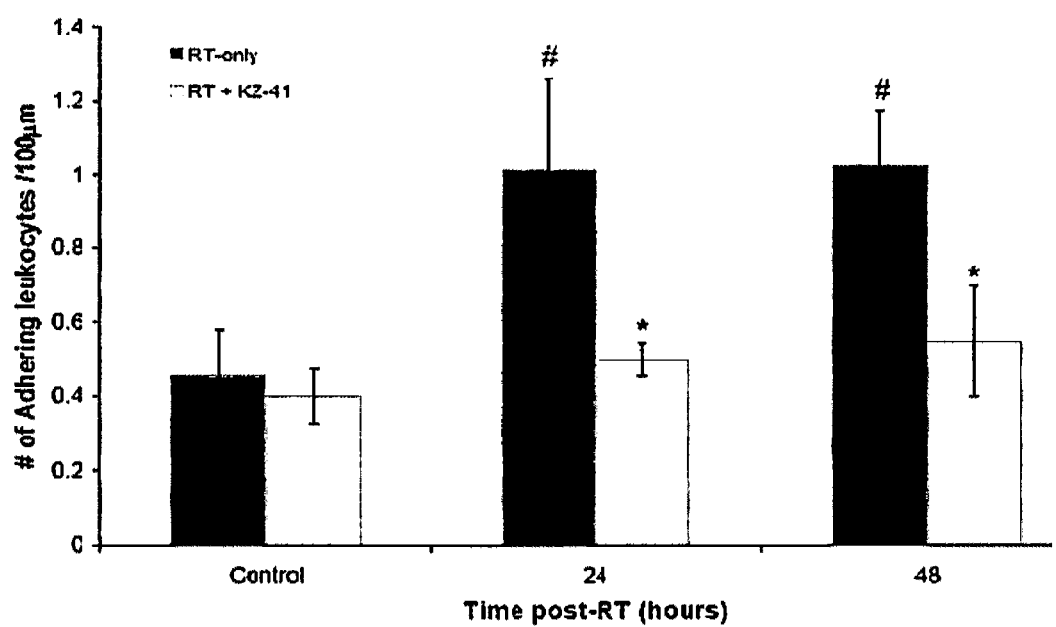
FIG. 13 is a graph illustrating leukocyte adhesion inhibition by KZ-41 following radiotherapy. Radiation induces an increase in adhering leukocytes in the pial vessels of the brain at 24- and 48-hrs following 20-Gy localized cranial irradiation. When the inflammatory response is limited via treatment with an antibody (anti-TNF or anti-ICAM) or with KZ-41, the increase in adhering leukocytes is inhibited. Percentage of adhering leukocytes per 100 μm is shown on the Y-axis. For each (control, 24-hr, 48-hr), the column on the left represents results after radiation treatment and the column on the right represents results after radiation treatment and administration of KZ-41.
Figure 14:
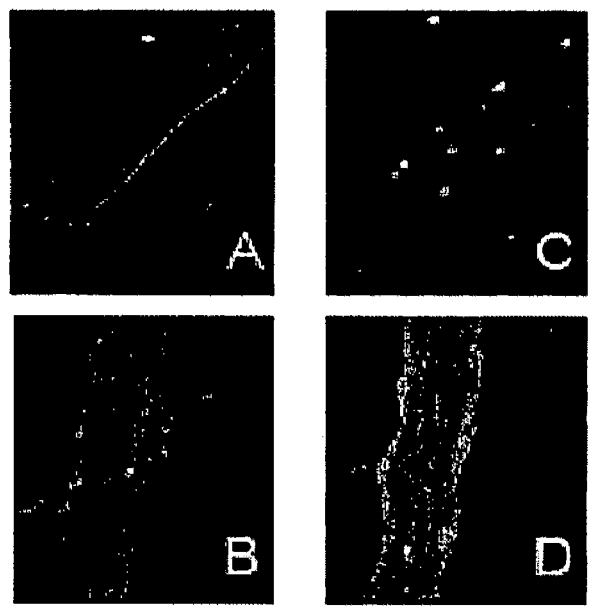
FIG. 14 is a series of images of radiation-induced leukocyte adhesion in the presence or absence of treatment with KZ-41. Representative images of the changes observed in leukocyte adhesion 24-hrs following radiation treatment (RT). (A-D) Control images with few adherent leukocytes observed (E) 24 hrs post-20Gy RT only; a significant amount of adhering leukocytes are visible. (F-H) 24 hrs post-20Gy RT+anti-TNF, RT+ICAM-1, and RT+KZ-41; when treated prior to radiation, the leukocyte adherence can be inhibited. Images were taken at approximately the same time after injection of Rhodamine-6G.
Figure 15:
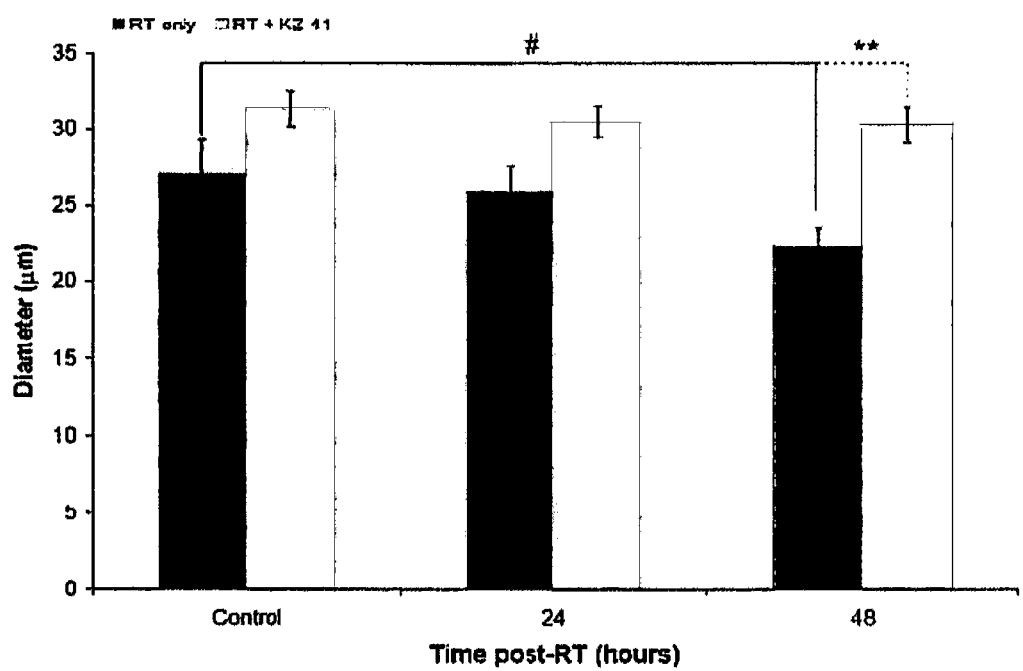
FIG. 15 illustrates radiation-induced changes in vessel diameter. Radiation induced a decrease in arteriole vessel diameter at 48-hrs following a single dose of 20-Gy localized cranial radiation. This decrease in vessel diameter is inhibited when the inflammatory response is limited via treatment with KZ-41. Diameter in μm is shown on the Y-axis.

Quinic acids are, however, catabolized by enzymes produced by gut bacteria. In rats, less than 10% of an orally-administered dose of quinic acid is recovered. The inventors therefore set out to produce quinic acid derivatives that retain or improve the beneficial effects of quinic acid, while being effective for oral administration. They discovered that amide substitutions such as, for example, carboxamide substitutions, produced compounds that retain the beneficial effects associated with quinic and shikimic acids, and in some cases provide a significantly improve effect, these same compounds being resistant to gut bacteria enzyme degradation. The compounds they have synthesized are not catabolized by bacterial enzymes, but are water-soluble, stable at room temperature, and effective for producing anti-inflammatory effects. As demonstrated by the graph in FIG. 12, the compounds may be administered orally to provide levels of compound in the tissue similar to, or better than, that produced by intravenous (IV) administration. These properties make the compounds especially useful as radioprotective and radiomitigant compositions, as it enables them to be easily shipped and stored, as well as easily self-administered.

The inventors have found these compounds generally relatively easy to synthesize, and they have found more than one approach for their synthesis, using combinations of steps generally known to those of skill in the art for molecular rearrangements or the addition of functional groups, as shown in the accompanying figures. In one example, synthesis of quinic acid analogs of the invention was performed by first forming the lactone. To the quinic acid starting material was added PTSA in refluxing benzene and DMF. To form the various individual analogs, the lactone was allowed to react with a variety of amines (see FIG. 1, R groups) in acetic acid at 85° C., as indicated in FIG. 1.

Figure 4:
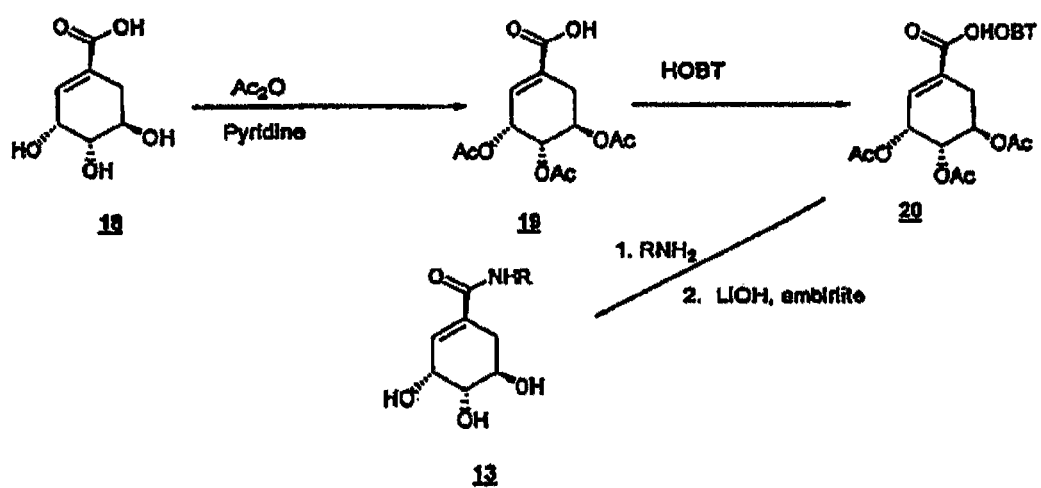
FIG. 4 is a scheme (Scheme 4) for the synthesis of compounds of the present invention.

Briefly, as shown in FIG. 4 (Scheme 4), compounds of the invention may be formed by protecting the alcohols of shikimic acid by converting them to acetates, followed by activation of the carboxylic acid moiety and treatment with propyl amine (R=nPr), followed by deacetylation with LiOH to give the desired amide.

Figure 5:
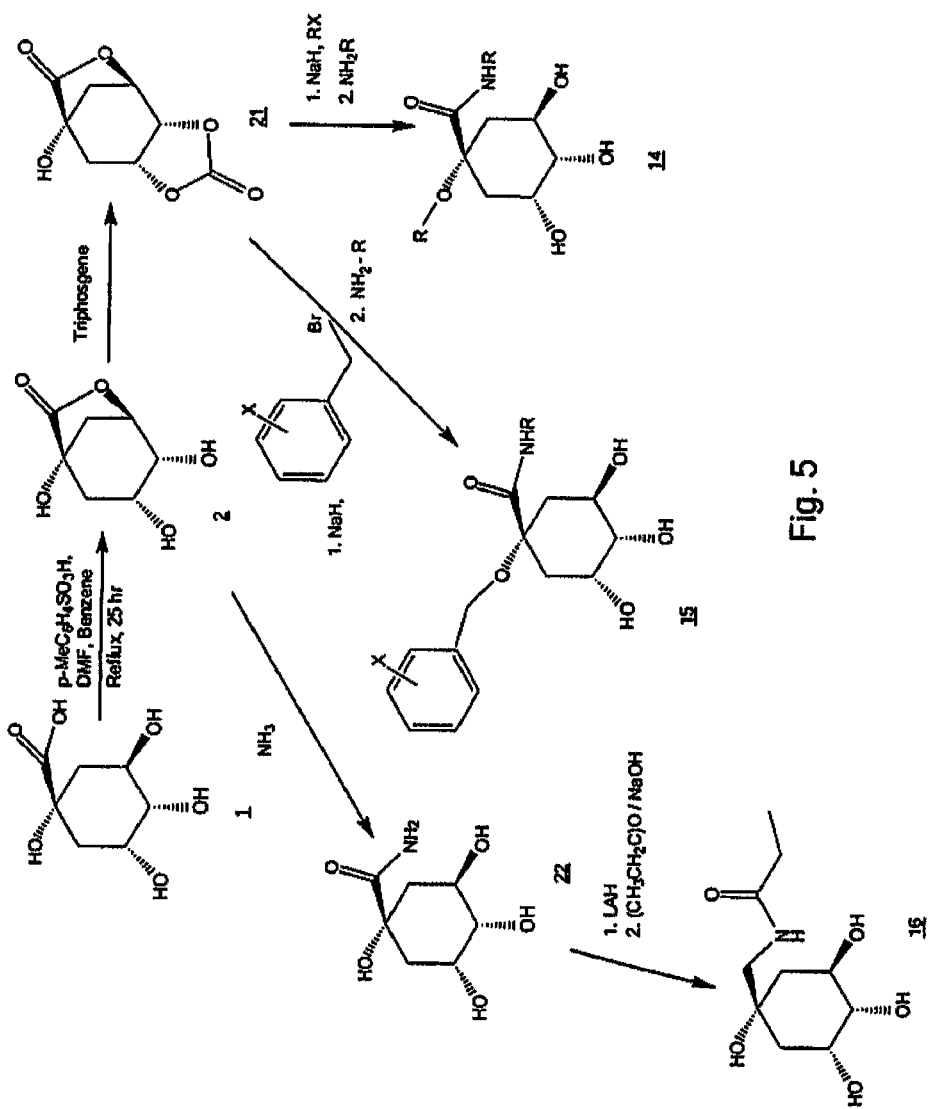
FIG. 5 is a scheme (Scheme 5) for synthesis of additional compounds, including amides compounds having a substitution at $R^3$.

Schemes for synthesis of additional compounds are described in FIG. 5 (Scheme 5). Briefly, compounds may be synthesized as shown, using chemistry previously described by Kaila, et al (Kaila, N., et at, (2005) *J. Med. Chem.* 48: 4346-4357), but with the addition of the indicated amines to improve the effects and the resistance to bacterial enzyme degradation.

Figure 6:
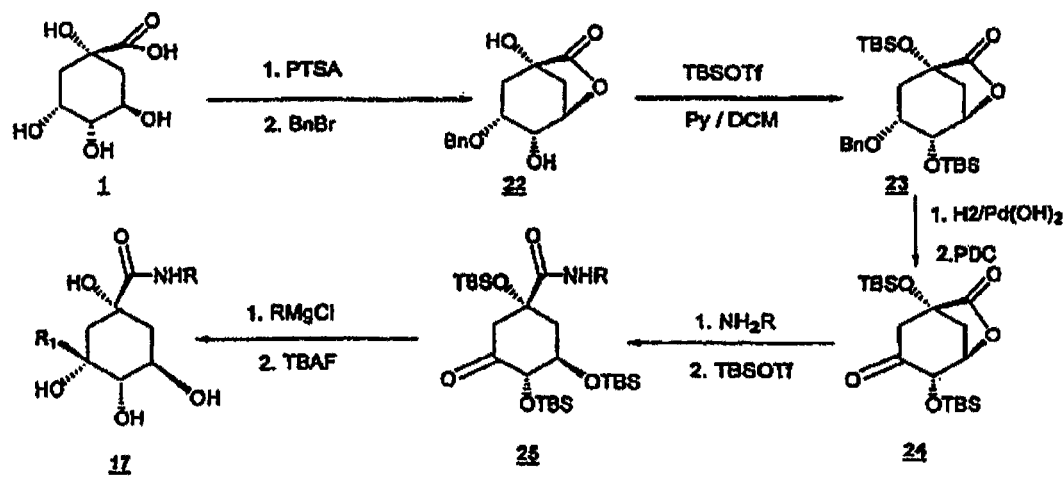
FIG. 6 is a scheme (Scheme 6) describing conditions for the synthesis of the tertiary alcohol analog of quinic acid.

The scheme for synthesis of the tertiary alcohol is shown in Scheme 6 (FIG. 6). It utilizes the formation of 22 from quinic acid, as outlined by Hanessian (Hanessian, S. et al. (1997) *J. Org. Chem.* 62: 465-473). The two alcohols are then protected by silyl protecting groups and the benzyl protecting group is removed to give the intermediate alcohol that is oxidized by pyridinium dichromate to give ketone 24. The epoxide may be opened with propyl amine (R=nPr) followed by silyl protection of the newly generated alcohol to give 25.

Compounds of the invention may be described by Formula I

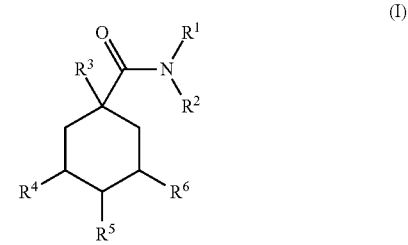

wherein:
$R^1$ and $R^2$ are each independently hydrogen, straight or branched alkyl, cycloalkyl, aryl, benzyl, arylalkyl, heterocyclic amine, aminoalkyl, ketone, or

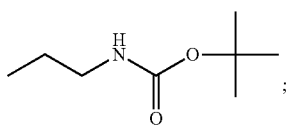

and
$R^3$, $R^4$, $R^5$, and $R^6$ are each independently hydrogen or hydroxyl.

In one aspect, $R^1$ and $R^2$ form a piperidine ring with N, and in another aspect of the invention is a compound such as compound KZ-41 wherein when $R^1$ or $R^2$ is hydrogen, the other of $R^1$ or $R^2$ is alkyl. In one aspect, the alkyl is —$C_3H_7$ and each of $R^3$-$R^6$ is hydroxyl.

In another aspect of the invention, the ketone may be

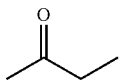

and each of $R^3$-$R^6$ may be hydroxyl.

Compounds of the invention may also comprise compounds of Formula I where $R^3$ is substituted with

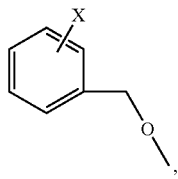

as well as compounds of Formula I where $R^3$ is absent and a double bond exists between carbons 1 and 6 of the ring.

Compounds of the present invention may conveniently be administered in a pharmaceutical composition containing the compound in combination with a suitable excipient. Such pharmaceutical compositions can be prepared by methods and contain excipients which are well known in the art. Such methods and ingredients may be found in *Remington's Pharmaceutical Sciences* (Alfonso Gennaro et al., eds., Lippincott, Williams & Wilkins, Baltimore, Md., 20th ed., 2000). Compounds and compositions of the present invention can be administered parenterally (for example, by intravenous, intraperitoneal or intramuscular injection), topically, orally, or rectally.

For oral therapeutic administration, the active compound may be combined with one or more excipients and used in the form of ingestible tablets, buccal tablets, troches, capsules, elixirs, suspensions, syrups, and wafers, for example. Such compositions and preparations should contain at least 0.1% of active compound. The percentage of the compositions and preparations may, of course, be varied and may conveniently be between about 2 to about 100% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. The active compound may also be incorporated into sustained-release preparations and devices.

Pharmaceutical dosage forms suitable for injection or infusion can include sterile aqueous solutions or dispersions or sterile powders comprising the active ingredient which are adapted for the preparation of sterile injectable or infusible solutions or dispersions. The ultimate dosage form should be sterile, fluid and stable under the conditions of manufacture and storage. The liquid carrier or vehicle can be a solvent or liquid dispersion medium comprising, for example, water, ethanol, a polyol (e.g., glycerol, propylene glycol, liquid polyethylene glycols), vegetable oils, nontoxic glyceryl esters, and suitable mixtures thereof. The proper fluidity can be maintained, for example, by the formation of liposomes, by the maintenance of the required particle size in the case of dispersions or by the use of surfactants.

Sterile injectable solutions can be prepared by incorporating the active compound in the required amount in the appropriate solvent with various other ingredients described above, followed by filter sterilization. The method of the invention has been shown to be effective for radioprotection and radiomitigation when the active agent is injected subcutaneously. One or more quinic acid and/or shikimic acid analogs may therefore be supplied in a prefilled auto-injector for subcutaneous injection and/or self-administration. Such auto-injectors are known to those of skill in the art and are frequently used to deliver medication which must be readily available, such as during asthma and/or severe allergy attacks. Commercially-available auto-injectors include, for example, the EpiPen® sold by Mylan, Inc. (Canonsburg, Pa. USA) and the TwinJect® device sold by Shionogi Pharma, Inc. (Atlanta, Ga. USA).

For topical administration, the present compounds may be applied in pure form in liquid compositions or administered as compositions or formulations, in combination with a dermatologically acceptable carrier, which may be a solid or a liquid.

Useful dosages of the compounds of formula I can be determined by comparing their in vitro activity, and in vivo activity in animal models. Methods for the extrapolation of effective dosages in mice, and other animals, to humans are known to the art (for example, see U.S. Pat. No. 4,938,949).

Another aspect of the invention is a method for administering to a human or animal patient a compound of the invention to provide an anti-inflammatory effect. Compounds of the invention have demonstrated anti-inflammatory effects both in vivo and in vitro. Of the compounds tested, several demonstrated efficacy for inhibiting NF-kB activity, with the N-propyl amide substitution (designated KZ-41) being especially effective. Compounds of the invention also demonstrated efficacy in decreasing leukocyte adhesion, as well as decreasing the levels or activity of a variety of cytokines known to contribute to inflammatory disease or diseases having a significant inflammatory component.

Therapeutically effective dosages may therefore be administered orally, or by IV or other appropriate means to achieve an anti-inflammatory effect. In one aspect, compositions of the invention may be administered to inhibit NF-kB activity for diseases such as, for example, rheumatoid arthritis. Compositions of the invention may also be effective for the treatment of viral illness, acute respiratory distress syndrome (ARDS), and other disease states associated with increased TNF-alpha and NF-kB activity.

The invention may be further described by means of the following non-limiting examples:

EXAMPLES

Synthesis of Specific QA Analogs

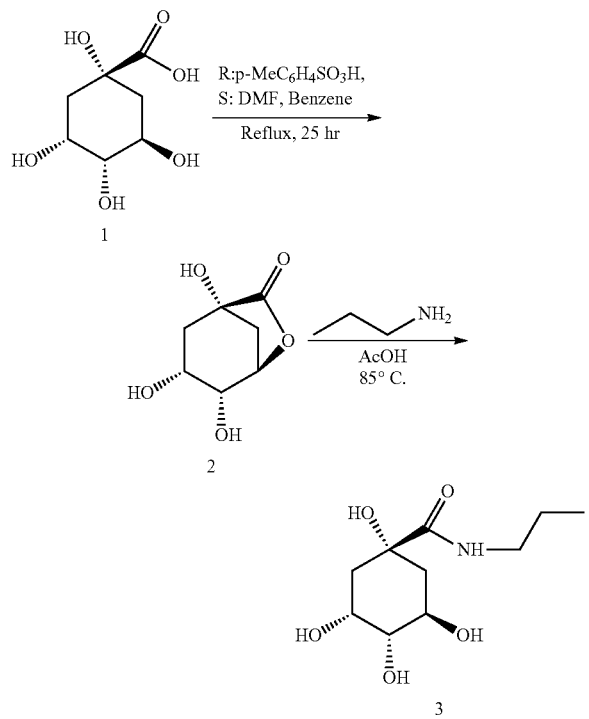

Scheme 9

1,3,4-Trihydroxy-6-oxa-bicyclo[3.2.1]octan-7-one (2). In a 200 ml round-bottom flask fitted with a stirring bar, reflux condenser, Dean-Stark trap, and argon inlet, 5 g of quinic acid (1, 26 mmol) was placed and 10 mL of dry DMF was added via syringe and the slurry stirred at room temperature. Next, benzene 60 mL and p-toluenesulfonic acid 0.5 g were added, and the slurry was heated to reflux for 26 h. TLC was used confirm the completion of reaction. A 1:1 mixture of EtOAc and 16eptanes (100 mL) was added to the cooled reaction mixture. The mixture was stirred for 1 h at room temperature and filtered. The collected solid was again stirred with a 1:1 mixture of EtOAc and 17eptanes (100 mL) for 1 hr at room temperature and filtered. Tituration was repeated one more time with a 1:1 mixture of EtOAc and 17eptanes (100 mL) and the precipitate collected to give 3.5 g of Lactone 2 (78% yield). Mp: 192-193° C., $R_f$ 0.25 (EtOAc); MS: [M-H]$^-$: 171; $^1$H NMR (300 MHz, DMSO) δ 1.72 (t, J=1.6 Hz, 1H), 1.82-1.88 (m, 1H), 2.07-2.13 (m, 1H), 2.25 (d, J=1.1 Hz, 1H), 3.49 (ddd, J=11.4, 6.3, 5.7 Hz, 1H), 3.82 (t, J=4.5 Hz, 1H), 4.61 (t, J=5.1 Hz, 1H), 4.816 (d, J=6.0 Hz, 1H), 5.23 (d, J=4.5 Hz, 1H), 5.89 (s, 1H).

1,3,4,5-tetrahydroxy-cyclohexane-carboxylic acid propylamide (3)

In a 50 mL round-bottom flask fitted with a stirring bar, reflux condenser, 0.196 g Lactone 2 (1.125 mmol), and propylamine (0.83 ml, 0.6 g, 10.13 mmol) were combined, then glacial acetic acid (0.19 ml, 0.20 g, 3.36 mmol) was added. The solution was warmed to 85° C. in an oil bath for 30 min, at which time TLC(CHCl$_3$:MeOH:NH$_3$OH=100:10:1) indicated complete consumption of the starting lactone. Reaction mixture was purified by flash column with the same solvent as TLC. Product 3 was collected, yielding 206 mg (80% yield). Mp: 132-133° C., $R_f$ 0.03 (CHCl$_3$:MeOH:NH$_3$OH=100:10:1); MS: [M-H]$^-$=232; $^1$H NMR (300 MHz, DMSO) δ 0.81 (t, J=6.0 Hz, 3H), 1.41 (ddd, J=13.8, 7.5, 6.9 Hz, 2H) 1.66-1.83 (m, 4H), 3.02 (dd, J=6.9, 6.6 Hz, 2H), 3.22 (t, J=6.0 Hz, 1H), 3.75 (ddd, J=13.8, 9.0, 5.7 Hz, 1H), 3.94 (s, 1H), 4.69 (d, J=4.5 Hz, 1H), 4.90 (d, J=5.4 Hz, 1H), 5.19 (d, J=3.6 Hz, 1H), 5.47 (s, 1H), 7.76 (t, J=5.4 Hz, 1H).

Scheme 10

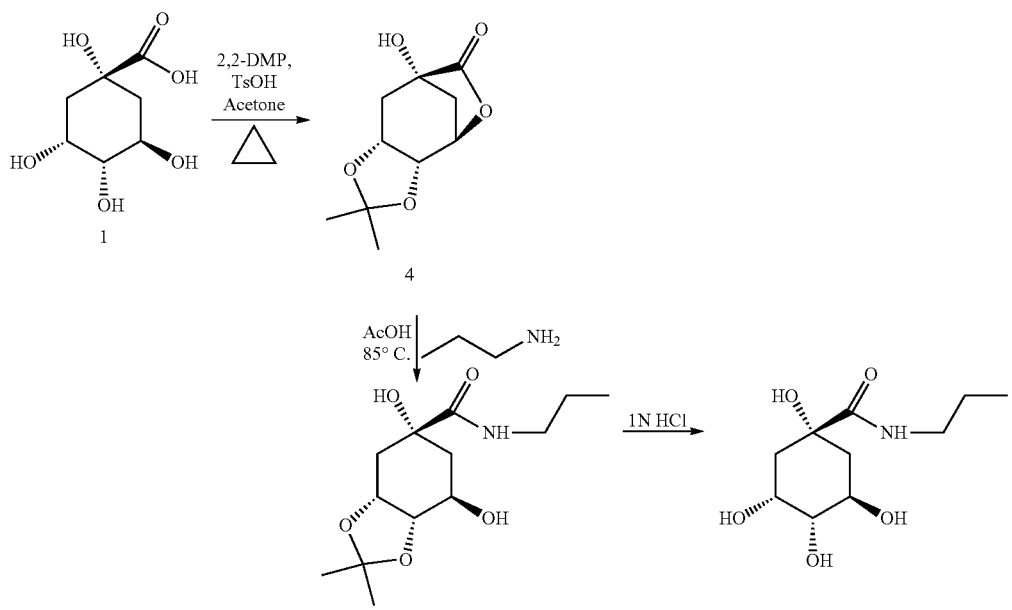

3,4-O-Isopropylidene-1,5-quinic Lactone (4)

A mixture of quinic acid (1)(20 g, 104.1 mMol), p-totuenesulfonic acid monohydrate (0.2 g), 2,2-dimethoxypropane (38 g, 364 mMol), and acetone (100 mL) was heated to reflux for 2 hr. The reaction mixture was cooled down, and solvent was removed under reduced pressure. The residue was dissolved in ethyl acetate (100 mL), washed with 5% aqueous sodium bicarbonate (100 ml). The aqueous phase was back-extracted with ethyl acetate (50×2 ml). The combined organic extracts were dried ($Na_2SO_4$), filtered, and the solvents were removed in vacuo. The residue was crystallized with hot ethyl acetate, got white solid 16 g (80% yield). mp: 147-149° C. $R_f$=0.3 (EtoAC:Hex=3:7). MS: $[M+Na]^+$=237. $^1$H NMR ($CDCl_3$) δ 1.37 (s, 3H), 1.55 (s, 3H), 2.21 (dd, J=14.7, 3.0 Hz, 1H), 2.30-2.44 (m, 2H), 2.68 (d, J=11.7 Hz, 1H), 2.83 (s, 1H), 4.32-4.36 (m, 1H), 4.51-4.58 (m, 1H), 4.79 (dd, J=2.6, 6.3 Hz, 1H).

5,7-Dihydroxy-2,2-dimethyl-hexahydro-benzo[1,3]dioxole-5-carboxylic acid propylamide (5)

Lactone (4), (10 g, 46.7 mMol), propylamine (30 mL), and glacial acetic acid (10 mL) was refluxed under argon with oil bath (85° C.) for 45 min. Solvents were removed under reduced pressure. The residue was washed with saturated sodium bicarbonate solution (100 mL), extracted with ethyl acetate (100×3 mL). The combined organic extracts were dried ($Na_2SO_4$), filtered, and the solvents were removed in vacuo. The residue was crystallized with hot ethyl acetate, got white solid 9.7 g (76% yield). mp: 85-86° C., $R_f$=0.15 (EtoAC:Hex=2:1). MS: $[M+Na]^+$=296. $^1$H NMR (DMSO) δ 0.83 (t, J=6.0 Hz, 3H), 1.24 (s, 3H), 1.38 (s, 3H), 1.40-1.45 (m, 2H), 1.61-1.64 (m, 2H), 1.72 (dd, J=14.7, 5.7 Hz, 1H), 2.04 (dd, J=14.7, 5.7 Hz, 1H), 3.01 (dd, J=6.6, 7.2 Hz, 2H), 3.80 (ddd, J=9.9, 6.3, 3.6 Hz, 2H), 4.31 (d, J=5.4 Hz, 1H), 5.01 (d, J=5.1 Hz, 1H), 5.28 (s, 1H), 7.73 (t, J=5.7 Hz, 1H).

1,3,4,5-tetrahydroxy-cyclohexane-carboxylic acid propylamide (3)

The amide (5) (5.0 g) was dissolved in water (10 mL), then added aq. 1M HCl (40 mL) at room temperature. The reaction mixture was stirred at room temperature for 1 hr. Solvent was removed under reduced pressure. Residue HCl was removed by adding EtOEt (20×3 mL) under vacuo. The residue was further dried under oil pump. Product (3) was collected, yielding product 4.26 g (100% yield). mp: 132-133° C., $R_f$ 0.03 ($CHCl_3$:MeOH:$NH_3OH$=100:10:1); MS: $[M-H]^-$=232; $^1$H NMR (300 MHz, DMSO) δ 0.81 (t, J=6.0 Hz, 3H), 1.41 (ddd, J=13.8, 7.5, 6.9 Hz, 2H) 1.66-1.83 (m, 4H), 3.02 (dd, J=6.9, 6.6 Hz, 2H), 3.22 (t, J=6.0 Hz, 1H), 3.75 (ddd, J=13.8, 9.0, 5.7 Hz, 1H), 3.94 (s, 1H), 4.69 (d, J=4.5 Hz, 1H), 4.90 (d, J=5.4 Hz, 1H), 5.19 (d, J=3.6 Hz, 1H), 5.47 (s, 1H), 7.76 (t, J=5.4 Hz, 1H).

Effects of Quinic Acid Amides on NF-kB Activity

The effects of the synthesized quinic acid analogs on NF-kB activity were assessed using a cell-based high-throughput screening system comprising A549 cells stably transfected with a plasmid containing a secreted alkaline phosphatase (SEAP) reporter gene driven by an NF-kB response element. Upon TNF-alpha stimulation, NF-kB translocates to the nucleus and binds the kappaB response element, causing transcriptional activation. This activation drives production of the SEAP reporter, which can be measured in the cell culture supernatant as a surrogate marker for NF-kB.

Figure 9:
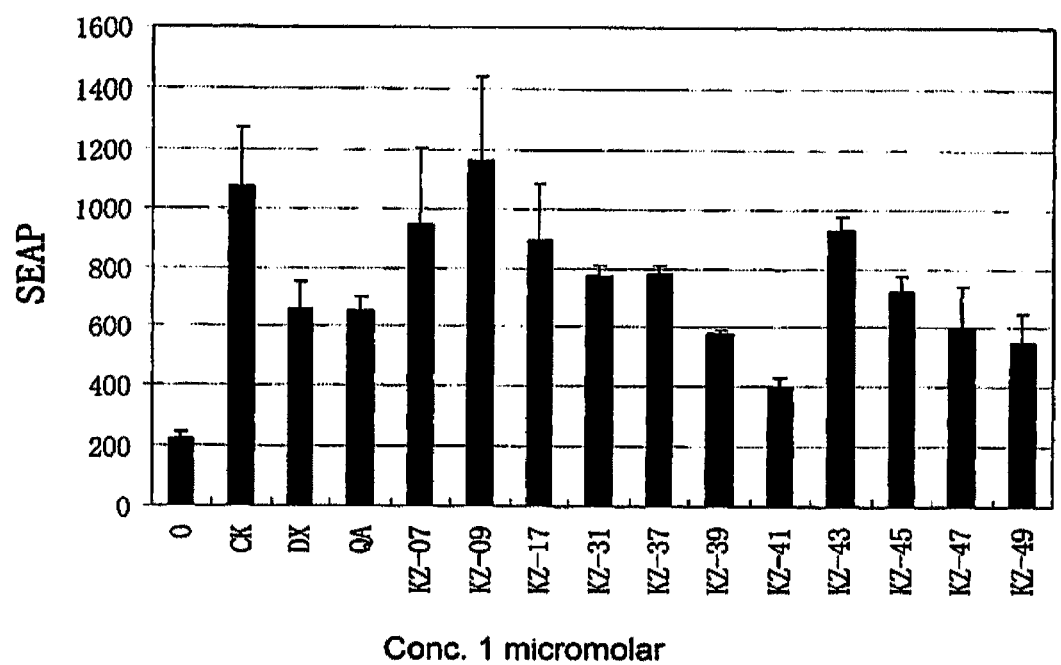
FIG. 9 is a graph illustrating the results of an SEAP assay performed using the indicated quinic acid analogs. The effects of the synthesized quinic acid analogs on NF-kB activity were assessed using a cell-based high-throughput screening system comprising A549 cells stably transfected with a plasmid containing a secreted alkaline phosphatase (SEAP) reporter gene driven by an NF-kB response element. Upon TNF-alpha stimulation, NF-kB translocates to the nucleus and binds the kappaB response element, causing transcriptional activation. This activation drives production of the SEAP reporter, which can be measured in the cell culture supernatant as a surrogate marker for NE-kB. Cells were plated on 24 well plates at $3\times10^4$ cells/well and allowed to grow overnight. A549 NF-kB SEAP reporter cells were treated with 10 ng/ml TNF-alpha and the quinic acid analog (1 micromolar) indicated on the x-axis. After 18 hours, SEAP activity (indicated on the y-axis) was measured.

Cells were plated on 24 well plates at $3 \times 10^4$ cells/well and allowed to grow overnight. A549 NF-kB SEAP reporter cells were treated with 10 ng/ml TNF-alpha and the quinic acid analog (1 micromolar) indicated on the x-axis of FIG. 4. After 18 hours, SEAP activity (indicated on the y-axis of FIG. 9 was measured.

Effect of Quinic Acid Amides on Leukocyte Activity

Figure 10:
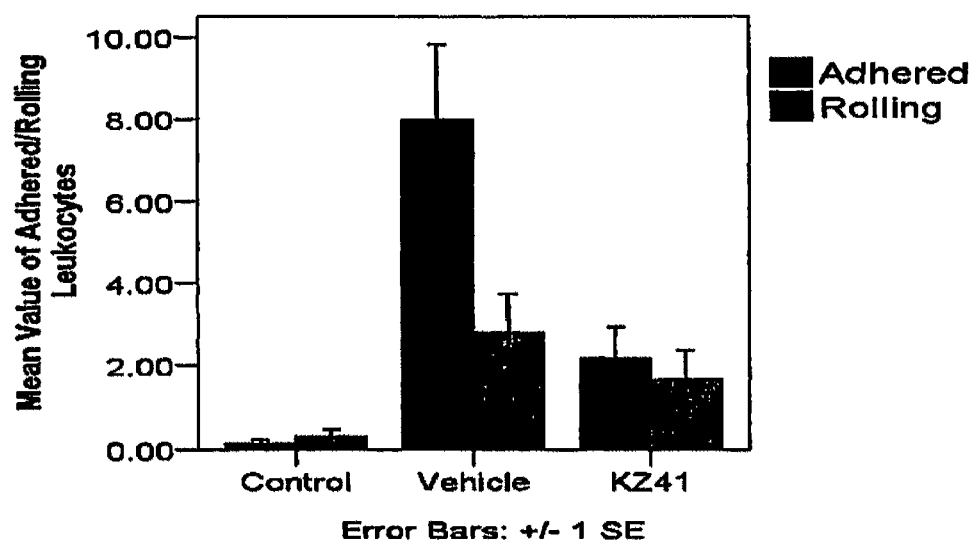
FIG. 10 is a graph illustrating the effect of quinic acid analog KZ-41 on leukocyte activity determined by the mouse dorsal flap model. Mean value of adhered vs. rolling leukocytes is indicated on the Y-axis. Error bars indicate +/−1 SE. For each pair of columns, the left column represents adhered and the right column represents rolling.

The effect of quinic acid analogs on leukocyte-endothelial cell interactions in response to LPS was also tested in a murine dorsal window imaging model. Briefly, animals were outfitted with imaging windows in the dorsal skin flap. Animals received systemic LPS and leukocyte rolling and adhesion were quantified four hours later. Rolling and adhesion were significantly increased in LPS-treated animals compared to vehicle alone (FIG. 10). Quinic acid analogs of the invention significantly reduced leukocyte adhesion, while having little effect on leukocyte rolling.

Male nude mice age 8-10 weeks, weighing 25-30 grams were used for the study. All surgical procedures were carried out aseptically. After the animal was anesthetized, a suitable area of skin on the dorsum was marked for hair removal with a clipper, followed by use of hair removal lotion. The surgical area was disinfected with alcohol and betadine. A thin dorsal skin fold was lifted from the back and sandwiched between two titanium plates. The titanium plates were firmly fixed with three screws and nuts through the holes made in the fold. The skin was sutured to the top of the plates for added stability. A circular section of the skin on one side of the skin fold, along with its cutaneous tissue and fascia was incised through the window of the assembly to expose the blood vessels and the striated muscle of the opposing skin of the dorsal skin fold. Antibiotic ointment containing bacitracin zinc, polymyxin B sulfate and neomycin sulfate was applied to the edges of the incised wound and a glass window fixed with a snap ring on top of the exposed area inside the dorsal skin fold assembly. Animals received buprenorphine (s.c. 0.1 mg/kg) immediately following surgery and every 12 hours for 48 hours for pain.

Quinic Acid Amides are not Degraded by Bacterial Enzymes

Experiments involving *Gluconobacter oxydans* were performed as described by Adachi et al. (Adachi, O., et al., (2003) *Biosci. Biotechnol. Biochem.* 67: 2124-2131). Briefly, *G. oxydans* (ATCC, Manassas, Va.) was cultured in basal media consisting of glycerol, 3 grams of yeast extract, and 1 gram of polypepton in 1 liter of tap water. In order to induce quinate dehydrogenase (QDH), quinate (2 g) was added and the pH adjusted to 7.0. Microorganisms were grown in medium (100 mL) at 30° C. For cell-mass production, a seed culture in 100 mL of medium was done overnight and transferred to 5 liters of fresh medium in a table top shaker incubator and cultivated for 12 hr under aeration. Harvested cells were suspended in medium (5 mM potassium phosphate and pH 6.5) and centrifuged to pellet cells. Cells were stored without freezing.

Cell suspensions were prepared by homogenizing harvested cells at a ratio of 10 g of wet cells per 10 mL of 5 mM potassium phosphate, pH 6.5. Cell suspensions were passed twice through a French pressure cell press. Intact cells were removed by low speed centrifugation and the cell-free extract was further centrifuged (68,000×g for 90 min) to separate the membrane and cytoplasmic soluble fraction. The membrane fraction was washed by homogenizing the precipitate in buffer and centrifugation repeated.

The membrane fraction (5 grams dried) was incubated with QA analogs (1 mM) under different pH conditions (pH 3-10) at 30° C. Culture media was sampled every 30 minutes for up to 3 hours. Three hours was chosen, as previous results have shown complete depletion of QA in this time frame (Adachi, et al. (2003) *Biosci. Biotechnol. Biochem.* 67: 2124-2131). Samples will be stored at −80° C. until analysis.

Samples were evaporated to dryness at 30° C. and reconstituted with 150 mL of 1:1 (v/v) mixture of 0.5% ammonia in water and acetonitrile. Internal standards were added to compensate for the variability of the mass spectrometric response. Prepared samples were injected onto the LC-MS/MS for analysis. The Shimadzu HPLC system (Shimadzu Scientific Instruments, Columbia, Md.) consisted of a SCA-10A vp system controller, two LC-10AD VP liquid chromatogram pumps, and a CTC PAL (CTC Analytics AG, Zwingen, Switzerland) autosampler. A Waters Nova-Pak® $C_{18}$ 3 mm (2.1× 50 mm) column protected by a 2-cm $C_{18}$ guard column maintained at ambient temperature was used in the analysis. The mobile phase A consisted of 0.5% ammonia in water and mobile phase B consisted of 0.5% ammonia in acetonitrile. The flow rate was set at 0.3 mL/min with a gradient from 60% to 40% A in 4 min, isocratic for 3 min, then returned to 40% in 2 min. MS/MS analysis was performed using a Sciex 3000 triple quadrupole mass spectrometer (Applied Biosystems, Foster City, Calif.). The mass spectrometry system was operated with turbo ionspray ionization source under negative ion mode. The spray needle voltage was set at 5,000 V, with the turbo gas temperature set at 400° C., and the declustering potential set at 60 V. For this study, samples were analyzed using a Q1 scan for product ion identification, a product ion scan for characterization of metabolites or enzymatic products and by using multiple-reaction monitoring (MRM) for quantitation of QA. Quantitation was performed using one set of MRM transitions: parent QA ions (MH⁻/191)® selective daughter ions m/z 127. A switch valve was used before the mass spectrometer to remove buffer matrix in the sample. The peak areas, peak ratios, linear regression, assayed concentrations, and other quantitative analysis calculations were conducted Sciex Analyst 1.4 software. A calibration curve, which is a weighted linear regression curve relating to peak area ratios of the analyte/internal standard to the concentration of analyte in the calibration standard, was established for each QA analog. The analyte concentrations in the samples was determined by comparison to the calibration curve using the Analyst software.

Figure 11:
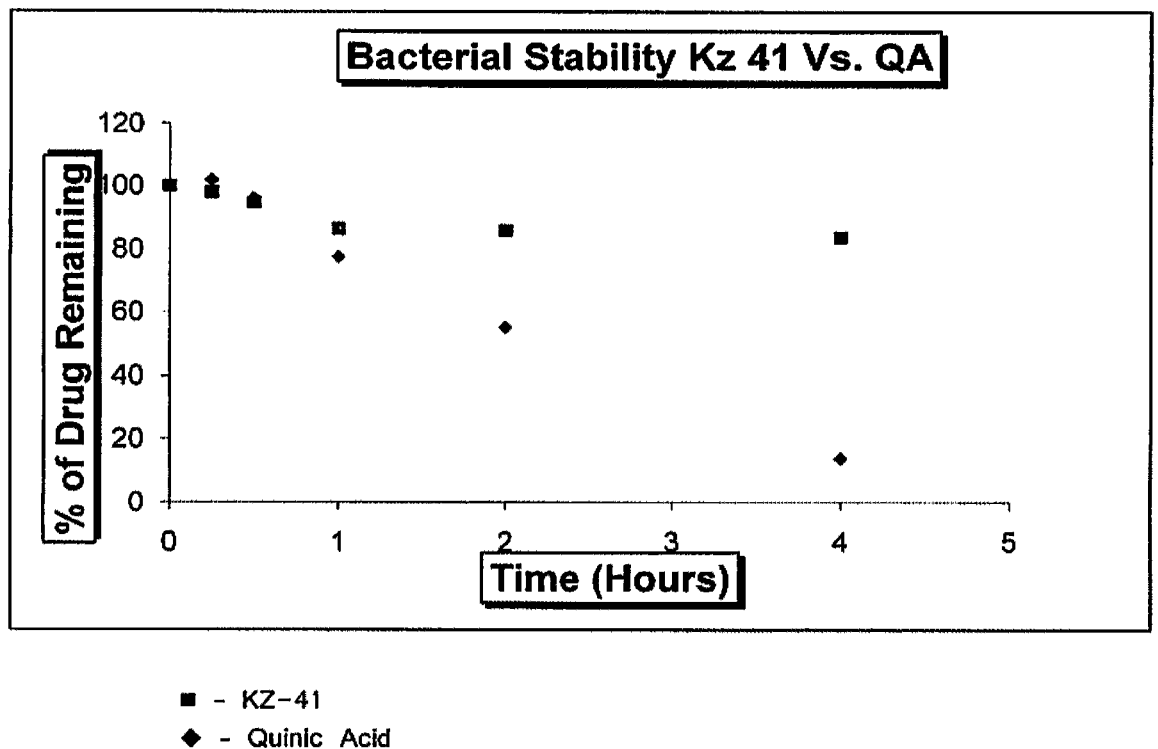
FIG. 11 is a graph illustrating the results of an assay to compare stability of analog KZ-41 with that of quinic acid (QA) to degradation by bacterial enzymes. Percentage of drug remaining is shown on the Y-axis and the time exposed to the enzymes is shown on the X-axis. Results for quinic acid are indicated by the diamonds (♦) and results for KZ-41 are indicated by the squares (■).

Results are shown in FIG. 11, where results for quinic acid are indicated by the diamonds (♦) and results for KZ-41 are indicated by the squares (■).

KZ-41 inhibits radiation-induced increases in the permeability of the blood brain barrier (BBB). Changes in BBB permeability were measured before and at 24- and 48-hrs post-radiation. Prior to radiation, BBB permeability was $13.14 \pm 1.99 \times 10^{-7}$ cm/s. At 24- and 48-hrs post-radiation permeability significantly increased to $20.30 \pm 2.36 \times 10^{4}$ cm/s ($P<0.05$) and $21.53 \pm 3.61 \times 10^{-7}$ cm/s ($P<0.05$), respectively. When treated with radiation and KZ-41, BBB permeability was significantly lower compared to radiation-only. At 24- and 48-hrs post-radiation the respective values were $14.56 \pm 0.36 \times 10^{-7}$ cm/s ($P<0.05$) and $14.67 \pm 0.66 \times 10^{-7}$ cm/s ($P<0.05$).

Leukocyte adhesion in pial venules was significantly lower in animals treated with radiation and KZ-41 versus radiation alone. Prior to radiation, leukocyte adhesion was $0.45 \pm 0.13$ adhering leukocytes/100 μm and was significantly increased compared to control at 24- and 48-hrs post-radiation: $1.01 \pm 0.25$ ($P<0.05$) and $1.02 \pm 0.15$ ($P<0.01$), adhering leukocytes/100 μm, respectively. In animals treated with radiation and KZ-41, there were significantly fewer adhering leukocytes at 24- ($0.5 \pm 0.05$ adhering leukocytes/100 μm; $P<0.05$) and 48-($0.55 \pm 0.15$ adhering leukocytes/100 μm; $P<0.05$) hrs post-radiation compared to radiation-only. No adhesion was observed in the arterioles. The presence of inflammation appears to create a period of vasoconstriction in the arterioles following radiation. Treatment with KZ-41 inhibited the radiation-induced inflammatory response effectively enough to inhibit this vasoconstriction. In the radiation-only group, there was a significant decrease in arteriole diameter at 48-hrs post-radiation ($22.45 \pm 1.16$ μm), compared to before radiation ($27.16 \pm 2.17$ μm). When treated with radiation and KZ-41 no decrease in arteriole diameter was observed, making the average arteriole diameter significantly larger at 48-hrs ($30.33 \pm 1.16$ μm; $P<0.01$) post-radiation in the radiation and KZ-41 treated group than in the radiation-only group ($22.45 \pm 1.16$ μm). There was no significant change in the diameter of the venules observed.

Figure 7:
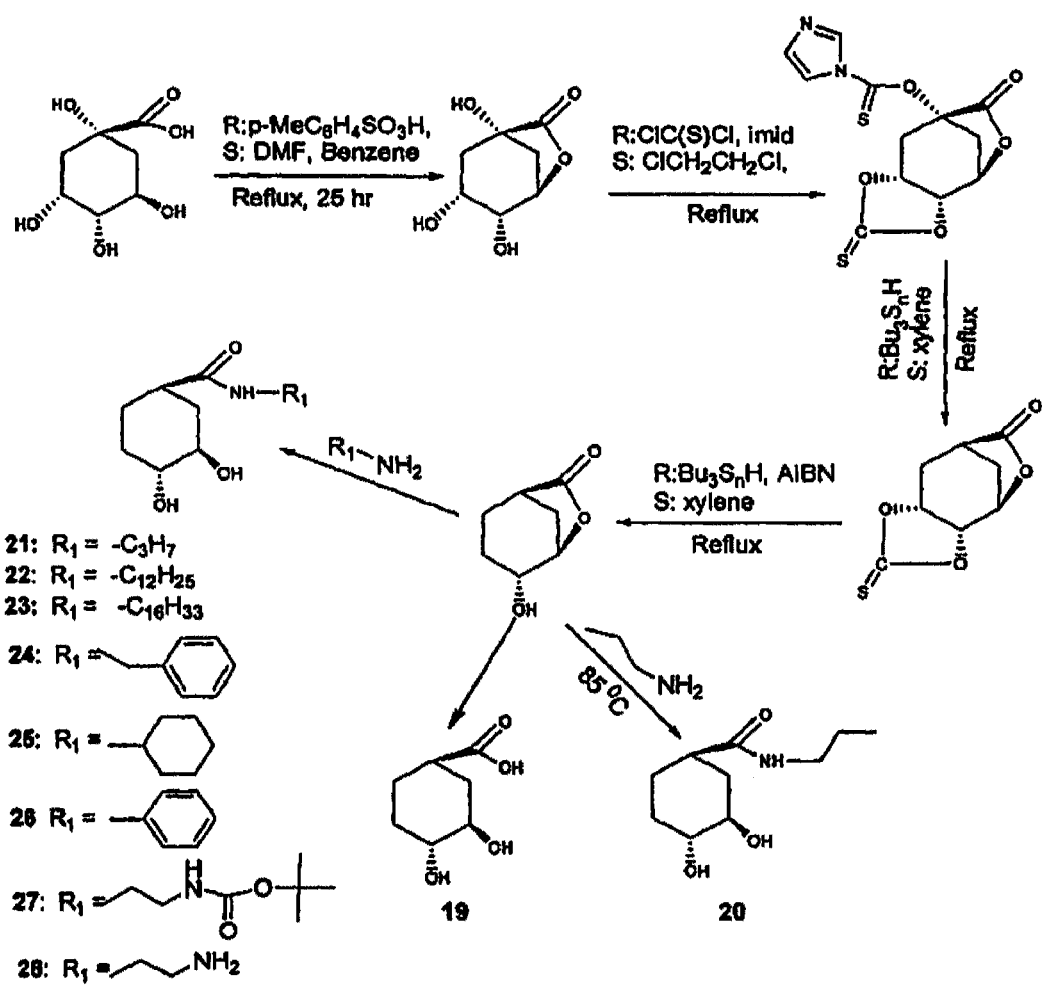
FIG. 7 is a scheme (Scheme 7) describing conditions for the synthesis of analogs wherein the hydroxyl at position $R^4$ has been removed
Figure 8:
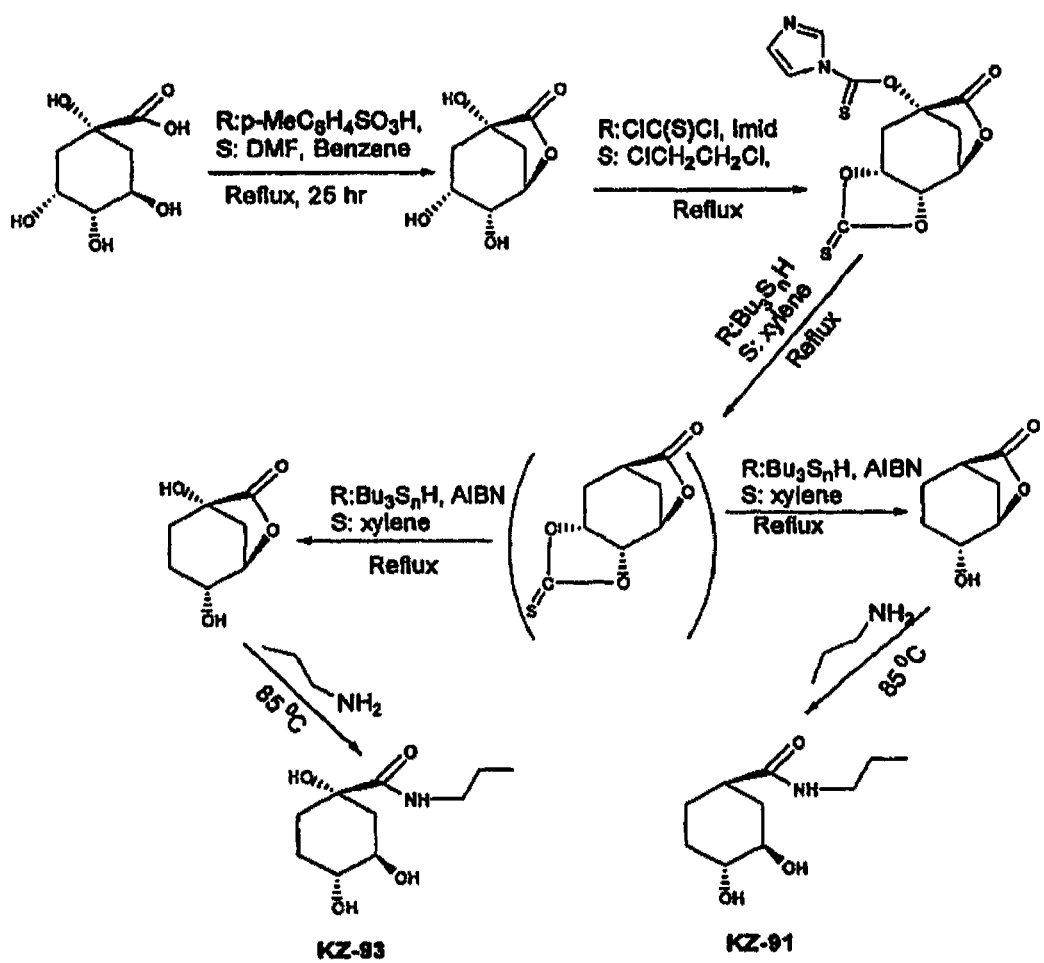
FIG. 8 is a scheme (Scheme 8) describing conditions for the synthesis of additional analogs KZ-93 and KZ-91.

Activated astrocytes are known to be a sign of injury in the brain. In addition astrocytes are known to secrete the inflammatory molecules TNF and ICAM-1. Therefore the relationship between the inflammation affecting the vasculature and the astrocytic response is of great interest. In the non-irradiated brain there were $11.41 \pm 1.21$ activated astrocytes/mm2, FIGS. 7 and 8. At 24- and 48-hrs post-radiation activated astrocyte counts were $21.92 \pm 0.24$ ($P<0.001$) and $22.92 \pm 0.36$ ($P<0.001$) activated astrocytes/mm2, respectively. In animals treated with radiation and KZ-41, the number of activated astrocytes was significantly greater than both the non-irradiated group and the radiation-only group. At 24- and 48-hrs post-radiation, the activated astrocytes counts were $33.69 \pm 0.55$ activated astrocytes/mm$^2$ and $34.38 \pm 0.41$ activated astrocytes/mm$^2$, respectively.

In the non-irradiated brain there is virtually no expression of TNF or ICAM-1 at the protein level, while there is expression in the irradiated brain at 24-hrs post-irradiation. When TNF antibody was administered in conjunction with radiation, immunofluorescence staining showed that both TNF and ICAM-1 protein expression was inhibited. When ICAM-1 antibody was administered in conjunction with radiation, ICAM-1 expression was inhibited, but TNF expression was not different than irradiated-only. Similarly, in the radiation and KZ-41 treated animals, there is minimal expression of ICAM-1 while TNF expression is most similar to the irradiated-only group.

Restoration of Thrombus Formation after Radiation/Vascular Injury

Mice were surgically fixed with dorsal windows for dermal vasculature imaging and were then allowed to recover for two days. Mice then received total body irradiation (TBI; 6 Gy, $^{137}$Cs; ~2 min) on Day 3. Various post-TBI injury time points were explored in order to determine the earliest time point at which TBI reproducibly affected thrombus formation. Post-capillary venule injury was induced at either 24, 48, 72, or 96 hours post-TBI followed by image acquisition at 5 min and 24 hr after injury to assess the primary endpoints, thrombus formation and blood flow restoration. It was determined that injury 72 hours post-TBI (i.e., day 6) was the earliest time point at which TBI reproducibly reduced thrombus formation. Blood flow restoration was assessed 24 hr later (i.e., day 7).

TBI significantly reduced thrombus formation and flow restoration in irradiated as compared to un-irradiated mice (1/6 vs. 5/6; p<0.05) The effect of KZ-41 (100 mg/kg i.p. administered 12, 36, and 60 hours post-TBI) on endpoints following injury at 72 hours post-TBI was compared to irradiated (0.9% N.S.) and un-irradiated controls. Thrombus formation in KZ-41-treated mice (7/8) was significantly higher than irradiated mice (p<0.05), but was no different than unirradiated mice (p>0.05). Results are shown in Table 1.

TABLE 1

| Group | Clot Formation | Flow Restoration |
| --- | --- | --- |
| Un-irradiated | 5/6 (83%) | 5/6 (83%) |
| Vehicle | 1/6 (17%) | 1/6 (17%) |
| KZ-41 | 7/8 (88%) | 3/7 (43%) |

Radiomitigation Effects

Figure 16:
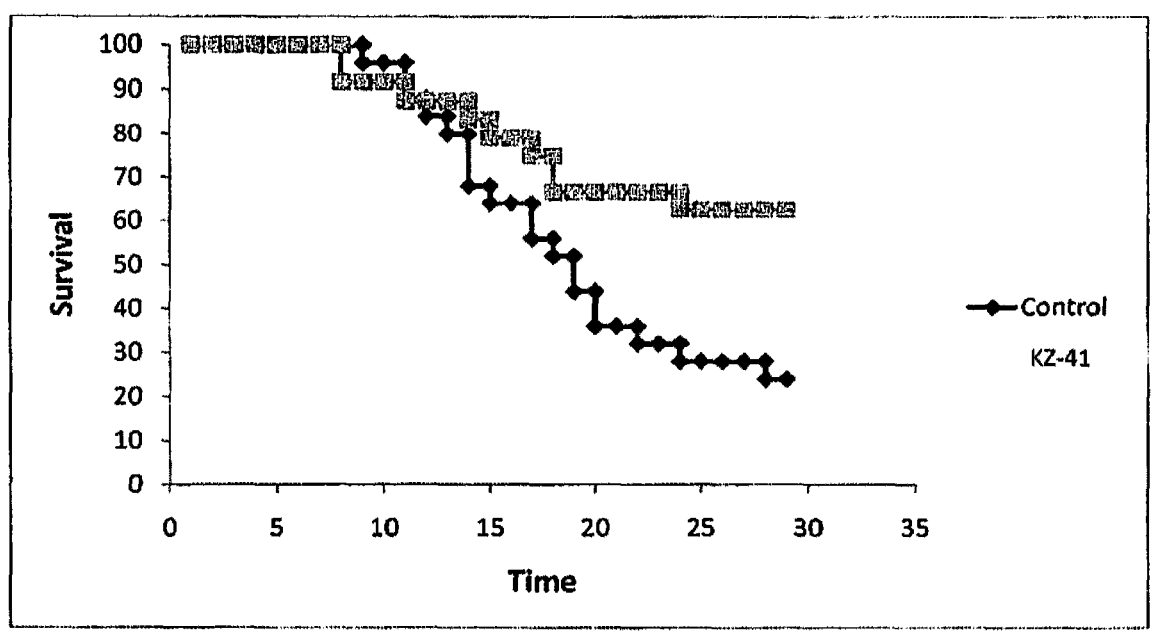
FIG. 16 is a graph illustrating results obtained when mice (C57BL/6) received total body irradiation (TBI; $LD_{80/30}$, $^{137}Cs$; ~2 min) followed by a single dose of KZ-41 (100 mg/kg in normal saline) administered subcutaneously 26 hrs after radiation exposure. KZ-41 (100 mg/kg) increased 30-day survival by a ≅45% compared to vehicle control (P<0.05). For each (control, 24-hr, 48-hr), the column on the left represents results after radiation treatment and the column on the right represents results after radiation treatment and administration of KZ-41.

Mice (C57BL/6) received total body irradiation (TBI) ($LD_{70/30}$), followed by administration of a single dose of KZ-41 (100 mg/kg in normal saline) 26 hours after radiation exposure. As shown in FIG. 16, 100 mg/kg KZ-41 increased 30-day survival by ≅45% compared to vehicle control (P<0.05).

What is claimed is:

1. A method for protecting a mammal from radiation injury, the method comprising administering to the cells a therapeutically effective amount of at least one compound of Formula (I)

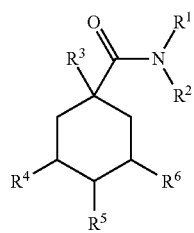

wherein:

$R^1$ and $R^2$ are each independently hydrogen, straight or branched alkyl, cycloalkyl, aryl, benzyl, arylalkyl, heterocyclic amine, aminoalkyl, ketone, or

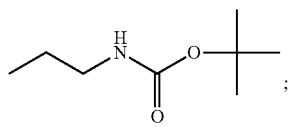

and $R^3$, $R^4$, $R^5$, and $R^6$ are each independently hydrogen or hydroxyl.

2. The compound of claim 1 wherein $R^1$ is hydrogen, $R^2$ is alkyl and $R^3$, $R^4$, $R^5$, and $R^6$ are each hydroxyl.

3. The compound of claim 2 wherein $R^2$ is —$C_3H_7$.

4. The compound of claim 1 wherein $R^1$ is cyclohexyl.

5. The compound of claim 1 wherein $R^1$ is aminoalkyl.

6. The method of claim 1 wherein the step of administering is performed prior to radiation exposure.

7. The method of claim 1 wherein the step of administering is performed after radiation exposure.

8. The method of claim 1 wherein the step of administering is performed by oral administration.

9. The method of claim 1 wherein the step of administering is performed by subcutaneous injection.

10. The method of claim 1, wherein the mammal is a human.

* * * * *